United States Patent [19]

Coon, deceased et al.

[11] 4,105,417
[45] Aug. 8, 1978

[54] FUEL ADDITIVE

[76] Inventors: Marvin D. Coon, deceased, late of Vallego, Calif., by John Hugh MacPherson, agent, 9 Anson Way, Kensington, Calif. 94707

[21] Appl. No.: 460,234

[22] Filed: Apr. 11, 1974
(Under 37 CFR 1.47)

[51] Int. Cl.² ............................................. C10L 1/22
[52] U.S. Cl. ................................. 44/63; 44/71; 44/72
[58] Field of Search .......... 44/72, 71, 63, 64; 260/482 C, 553 A

[56] References Cited

U.S. PATENT DOCUMENTS

| | | | |
|---|---|---|---|
| 2,373,372 | 4/1945 | Banks | 44/71 |
| 2,438,452 | 3/1948 | Pollock | 260/482 C |
| 2,649,473 | 8/1953 | Chenicek | 260/482 C |
| 2,677,698 | 5/1954 | Deutschman, Jr. et al. | 260/482 C |
| 2,772,148 | 11/1956 | Brehm et al. | 44/71 |
| 3,139,330 | 6/1964 | Malec | 44/72 |
| 3,448,049 | 6/1969 | Preuss et al. | 260/482 C |
| 3,454,555 | 7/1969 | van der Voort et al. | 44/72 |
| 3,574,576 | 1/1974 | Honnen et al. | 44/72 |
| 3,615,294 | 10/1971 | Von Allmen | 44/71 |
| 3,652,240 | 3/1972 | Dorn et al. | 44/71 |
| 3,684,713 | 8/1972 | Piccolini | 44/64 |
| 3,897,224 | 7/1975 | Chandler | 44/71 |

*Primary Examiner*—Daniel E. Wyman
*Assistant Examiner*—Mrs. Y. Harris-Smith
*Attorney, Agent, or Firm*—C. J. Tonkin; J. Tedd Brooks

[57] ABSTRACT

A certain fuel-soluble nitrogen-hydrocarbyl-substituted nitrogenous composition has been found to display a previously unreported detergency in the internal combustion engine when present in fuels to the extent of 10–4,000 ppm. The nitrogenous composition is composed of a hydrocarbyl group bonded to a nitrogenous substrate. The hydrocarbyl substituent contains from 30 to about 400 carbon atoms, and the nitrogenous substrate is a carbamate, urea or amide.

3 Claims, No Drawings

FUEL ADDITIVE

BACKGROUND OF THE INVENTION

Field of the Invention

Modern research into fuel compositions for the internal combustion engine has for its principal goal the promotion of longer engine life with less maintenance and better performance. This goal is partly achieved by the use of fuel additives which cleanse the carburetor and intake valves and help to maintain their cleanliness. Honnen and Anderson in U.S. Pat. No. 3,348,757 disclosed the use for this purpose of certain hydrocarbyl polyamines as fuel additives.

SUMMARY OF THE INVENTION

A fuel additive is provided for liquid fuel compositions and fuel concentrates which is effective in intake valve deposit control and maintaining carburetor cleanliness. The additive consists of certain fuel-soluble nitrogen-hydrocarbyl-substituted nitrogenous compounds composed of a hydrocarbyl substituent containing at least 30 and up to a about 400 carbon atoms, bonded to a nitrogeneous substrate which imparts desired properties to the nitrogenous composition as a fuel additive. The nitrogenous substrate is either a carbamate, urea, or amide. The additive is present in the liquid hydrocarbon fuel in amounts of from 10 to 70 weight percent.

DETAILED DESCRIPTION OF PREFERRED EMBODIMENTS

A fuel additive, and fuel composition containing a major amount of a liquid hydrocarbon fuel and 10–4,000 ppm of said additive, wherein said additive consists of a hydrocarbyl-substituted nitrogenous composition composed of a hydrocarbyl group of 30–400 carbon atoms bonded to a nitrogenous substrate which is either a certain carbamate, urea, or amide. The additive is effective in intake valve deposit control.

HYDROCARBYL SUBSTITUENT

Hydrocarbyl, as used in this invention, denotes an organic radical composed of carbon and hydrogen which may be aliphatic, alicyclic, aromatic or combinations thereof, e.g., aralkyl. Elements other than carbon and hydrogen, such as oxygen, or chlorine, form a minor, insubstantial, sometimes adventitious, component of a hydrocarbyl group. Preferably, the hydrocarbyl group will be relatively free of aliphatic unsaturation, i.e., ethylenic and acetylenic, particularly acetylenic unsaturation.

The hydrocarbyl group in the nitrogen-substituted nitrogenous compound will contain at least 30 carbon atoms and preferably less than about 400 carbon atoms. The hydrocarbyl group is preferably of 30–300 and more preferably 50–300 carbon atoms and most preferably has in excess of 65 carbon atoms. The hydrocarbyl groups are preferably aliphatic having preferably from 0 to 2 sites of ethylenic unsaturation and most preferably from 0 to 1 such site. Hydrocarbyl groups derived from a polyolefin, itself derived from olefins (normally 1-olefins) of from 2 to 6 carbon atoms with the proviso that ethylene is copolymerized with a higher olefin (i.e., ethylene being copolymerized with an olefin of at least 3 carbon atoms), or from a high molecular weight petroleum-derived hydrocarbon, are preferred, and of these polyisobutene is most preferred. Illustrative sources for the high molecular weight hydrocarbyl substituents are: petroleum mineral oils and polyolefins, such as naphthenic bright stocks, high viscosity index paraffins, neutral oils, polypropylene, polyisobutylene, poly-1-butene, copolymers of ethylene and propylene, poly-1-pentene, poly-4-methyl-1-pentene, poly-1-hexene, poly-3-methylbutene, etc.

The nitrogen-hydrocarbyl-substituted nitrogenous compound is preferably derived from the reaction of the halogenated hydrocarbon with a certain nitrogenous substrate in the desired mol proportions, usually from about 1:4 to about 2:1. It is normally preferred that excess nitrogenous substrate be used, and mol ratios of hydrocarbyl halide to nitrogenous substrate of about 1:1–4 are preferred. The hydrocarbyl halide is prepared from the hydrocarbon by halogenation, ionically or free-radically, by addition or allylic substitution. The hydrocarbon may be prepared by polymerization of olefins of from 2 to 6 carbon atoms to produce a polyolefin of the desired molecular weight. The method of halogenation and subsequent reaction of the hydrocarbyl halide has been previously described in U.S. Pat. Nos. 3,565,804 and 3,671,511, and is illustrative of a synthesis of the nitrogen-hydrocarbyl-substituted nitrogenous composition from a hydrocarbyl halide and a nitrogenous substrate.

To provide for reaction with the hydrocarbyl halide in forming the nitrogen-hydrocarbyl-substituted compound of the present invention, it is required that the nitrogenous substrate before reaction with the hydrocarbyl halide contain at least one primary or secondary amino nitrogen atom. The reaction with halogenated hydrocarbon performed under preferred conditions (e.g., as in above cited patents) is not believed to produce appreciable amounts of di- or poly- substituted hydrocarbon, rather, it is believed that each hydrocarbyl group is monovalently substituted to a particular nitrogen atom of the nitrogenous substrate.

The hydrocarbyl substituents in the nitrogen-hydrocarbyl-substituted compound can be found at any nitrogen atom which is capable of receiving it. The nitrogen atoms, in general, are inequivalent by symmetry so that the substituted nitrogenous compounds which find use in this invention are mixtures of mono- and polyhydrocarbyl substituted compounds with hydrocarbyl groups substituted at various equivalent and inequivalent nitrogen atoms and could be denoted N-hydrocarbyl, N,N'-dihydrocarbyl, etc., but for simplicity are simply called nitrogen-substituted. The same can be said of N-hydroxy, N-alkyl and N-hydroxyalkyl substituents in nitrogenous substrates containing same.

The molecular weights used herein are number average molecular weights. To obtain an average carbon number from the average molecular weight of the hydrocarbon, divide by 14 which represents the weight of $CH_2$. In many instances a single compound will not be used as a reactant in the preparation of the compositions of this invention. The molecular weight or carbon number reported for the hydrocarbyl substituents are usually average values of a rather sharply peaked distribution. Also, as stated previously, when the nitrogens are inequivalent, substitution of the various groups on different nitrogens provides different isomers as does isomeric branching. The number of hydrocarbon substituents need not be a whole number when averaged over a total composition since generally, a mixture will be obtained containing mono-, di-, and tri- or higher substituted molecules averaging out to a fractional or whole number.

NITROGENOUS SUBSTRATE

In this section, the particular nitrogenous substrates which upon nitrogen-hydrocarbyl-substitution yield the fuel additives of the present invention are described. The nitrogenous substrates are materials known to the art. A comprehensive exposition of the chemistry, method of preparation and literature of these nitrogenous materials is found in Sidgwick's "The Organic Chemistry of Nitrogen," Clarendon Press, Oxford, 1966, and in Noller's "Chemistry of Organic Compounds," Saunders, Philadelphia, 2nd Ed. 1957.

The nitrogenous substrate imparts desirable and useful properties to the high molecular weight hydrocarbyl substituent as a fuel additive; e.g., properties such as basicity, rust and corrosion inhibition, thermal or oxidative stability of fuel composition and dispersancy. Viewed in another way, the high molecular weight hydrocarbyl substituent is found to increase the effectiveness of the nitrogenous substrate as a detergent fuel additive without diminishing its other desirable properties. It is a preferred embodiment of the present invention that the nitrogenous compositions be used in combination with each other and other fuel additives to achieve maximum performance at minimum cost.

The carbamate, urea or amide which finds use within the scope of the present invention as a nitrogenous substrate is preferred for special thermal or oxidative stability and is typified by the presence of at least one and no more than two O=C groups in its structure, as, for example, in the amide, carbamate and urea of the non-limiting structural formula $O=C(OR)_a(NHR)_bR_c$, wherein R is H or $C_1$-$C_{10}$ alkyl, aryl, hydroxyalkyl or amino alkyl, and $a = 0,1$, $b = 1,2$ and $c = 0,1$, with $a + b + c = 2$ and each R is the same or different. A nitrogenous substrate in this group encompasses for example alkyl carbamate, urea and N-alkyl urea, aminoethyl urea, 1-aminoethyl-2-oxoimidazolidine, 1-aminopropyl imidazoledione, aminoethylacetamide, aminoethylphenylurea, bis-ethylenephenylurea, N-(hydroxymethyl) urea, urethane, cyclobiuret (diazodicarboximide), and biuret. The carbamate, urea and amide will, in general, contain from 1 to about 6 nitrogen atoms and from one to about 50 carbon atoms. For example, Sidgwick's text (ibid) and Noller's "Chemistry of Organic Compounds," 2nd Ed., Saunders (especially Chapters 15 and 12), present the chemistry and method of preparation of this useful nitrogenous substrate. The preferred method of producing the nitrogen-hydrocarbyl-substituted nitrogenous compound having as a nitrogenous substrate a carbamate or urea is to react a nitrogen-hydrocarbyl-substituted amine with phosgene. The reaction of 2 mols of amine with phosgene yields the urea. The reaction of 1 mol of amine and 1 mol of alcohol with phosgene yields the carbamate. Alternatively, the amine is reacted with an alkyl, aryl or alkaryl isocyanate to obtain the substituted urea, and the molar ratio of isocyanate to amine is used to control the number of urea functionalities introduced into the amine. The preferred method for the nitrogen-hydrocarbyl amide is by reaction of a nitrogen-hydrocarbyl-substituted amine with an acyl halide or by reaction of the hydrocarbyl halide with the amide. The nitrogen-hydrocarbyl-substituted urea is distinguished by its water tolerance in addition to its detergency in the internal combustion engine as a fuel additive and hence is often preferred when water tolerance of the fuel composition is important. "Water tolerance," as the term is used here, means the allowing of good water separation from a fuel composition after contact with same, U.S. Pat. No. 3,746,520.

The fuel additives of the present invention are preferred and chosen for specific fuel compositions with a view to the required fuel characteristics and the operating conditions of the engine. An additive is preferred if it passes the harm tests measuring water tolerance, filter plugging, particulate suspension, rust and corrosion, additive compatibility, toxicity, octane depreciation, bearing corrosion, anti-icing, lubricating oil compatibility, fuel system material compatibility or paint deterioration.

Particular preferred additives are selected for compatibility with unleaded fuel (i.e., fuel containing less than 0.1 g of lead per gallon), inhibition of pre-ignition, inhibition of octane requirement increase, water shedding (i.e., water tolerance), inhibition of crankcase sludge following normal blow-by, combustion chamber deposit control, anti-rusting, or dispersancy.

The most preferred additives of the present invention would be those which effect a reduction or control of hydrocarbon or carbon monoxide emissions, display carburetor detergency, intake valve deposit control, or are compatible and beneficial to exhaust gas recirculaton systems (EGR) or early fuel evaporation systems (EFE) cleanliness.

COMPOSITIONS

Depending upon the particular application of the additive of this invention, its synthesis may be carried out in the medium in which it will ultimately find use, and it may be formed in concentrations which provide a concentrate of the additive. Thus, the final composition may be in a form to be used directly upon dilution in fuels or fuel concentrates. The additive of this invention is generally employed in hydrocarbon liquid fuels. It may be formulated as a fuel concentrate using a suitable solvent, preferably an aromatic hydrocarbon solvent such as benzene, toluene, xylene or other low boiling aromatic thinner. Aliphatic alcohols or alkoxylated alcohols of about 3-8 carbon atoms such as ethylene glycol, isopropanol, isobutanol, n-butanol, 2-ethyl hexanol and the like are also suitable for use with the additive. Other polymeric materials may also be used in conjunction with the additive of this invention, e.g., polyisopropylene, or polyoxyalkylene glycol.

The liquid hydrocarbon fuels of the present invention encompass fuels boiling in the gasoline and diesel oil range, e.g., having ASTM D-86 90% points from about 200° F (93° C) to about 700° F (371° C) and generally boiling from about 100° F (38° C) to about 750° F (399° C).

In the fuel, the concentration of the additive will generally be at least 10 ppm and usually not more than 4,000 ppm, more usually in the range of from about 50 to 1,500 ppm. In fuel concentrates, the additives will range from about 1-90 weight percent, more usually from about 5 to 70 weight percent and generally not exceeding 80 weight percent. In gasoline fuels, other fuel additives may also be included such as antiknock agents, e.g., tetramethyl lead, tetraethyl lead; also included may be lead scavengers such as arylhalides, e.g., dichlorobenzene or alkyhalides, e.g., ethylene dibromide; and antioxidants such as alkylated phenols or aromatic amines. A non-volatile lubricating mineral oil, e.g., petroleum spray oil, particularly a high VI refined paraffinic or naphthenic lubricating oil, having a viscosity at 100° F (38° C) of 80-2000 SUS is a suitable oil-additive for the gasoline composition when used with the additives of the present invention. Polymeric materials as mentioned above, such as polyolefins and glycols, e.g., polypropylene glycol, can also be used. These materials are believed to act as a carrier for the additive and assist in removing and preventing deposits. They are employed in amounts of from about 0.05 to 0.5 percent by volume based on the final gasoline composition.

EXAMPLE A

Polyisobutenyl diethyldiazodicarboxylate wherein the polyisobutenyl is of 950 average MW (50 g, about 0.44 mol) was dissolved in 50 ml of benzene. Diethylenetriamine (6.2 g, 0.06 mol) was added and solvent removed by distillation until the temperature reached 150° C. Heating and stirring were continued for 3.5 hours at 150°-165° C. The mixture was cooled, dissolved in a mixture of benzene, hexane, and a small quantity of n-butanol and washed twice with water. The washed product (polyisobutenyl-cyclobiuret) was concentrated by distillation, removing water by azeotroping and stripped on the solvent stripper to yield 25 g of slightly hazy material: N, 3.25%; MW 1041; IR, 1580 (amide); 1700 cm$^{-1}$ (imide).

EXAMPLE B Polyisobutenylaminoethyl phenyl-urea was made by adding phenyl isocyanate (8.2 g, about 0.069 mol) in 20 ml of benzene dropwise with stirring to polybutenylethylene diamine (about 0.069 mol) over a 5-minute period. The temperature rose to 45° C. The mixture was heated to 100° C, then transferred to another flask for stripping on the solvent stripper to yield 119.9 g of material: N, 2.18%; MW 1697; IR, 3300 (NH), 1650 cm$^{-1}$ (CONH$\overset{\frown}{2}$). The polyisobutenyl substituent was of 1,400 average molecular weight.

EXAMPLE C

Polyisobutenyl bis-ethylene phenylurea was made by adding phenyl isocyanate (24.6 g, about 0.207 mol) in 60 ml of benzene with stirring to polyisobutenyl ethylene diamine (about 0.069 mol) over a 5-minute period causing the temperature to rise to 45° C. The mixture was heated to 100°-110° C for 40 minutes then cooled and 10 ml of methanol added to destroy any unreacted isocyanate. The mixture was reheated to 100° C for 15 minutes then cooled and washed twice with 200-ml portions of water. Stripping on the solvent stripper yielded 131 g of product: N,2.81%; MW about 1320; IR, 3300 (NH), 1650 cm$^{-1}$ (C=O, broad). The polyisobutenyl substituent was of 1400 average molecular weight.

EXAMPLE D

N-polyisobutenyl acetamide of ethylene diamine was made from the reaction of polyisobutenyl chloride with monoacetylethylenediamine. 250 grams of polyisobutenyl chloride of average molecular weight about 1400 was mixed with 41 grams of monoacetylethylenediamine in 200 ml of xylene. The mixture was heated to reflux with stirring for about 3½ hours. The mixture was cooled, diluted with hexane and washed with 500 ml of 10% sodium hydroxide solution. The product was then washed three times with a 500 milliliter portion of 60% water, 30% mixture ethyl alcohol and 10% isobutanol. The stripped product was found to contain 0.83% N.

EXAMPLE E

Polyisobutenyl-1-aminoethyl-1-oxoimidazolidine, classified as a cyclic urea, was produced from the reaction of polyisobutenyl chloride with 1-(beta-aminoethyl)-2-imidazolidone. 280 grams of polyisobutenyl chloride of average molecular weight about 1,400 was mixed with 90 grams of the imidazolidone in 300 ml of xylene and 200 ml of 4-methylpentanol. The mixture was heated to reflux with stirring at 134° C for about 6 hours. The product was diluted with hexane, washed with 500 ml of 10% sodium hydroxide solution, and washed twice with 500 milliliter portions of a 60% water, 30% alcohol and 10% isobutanol solution. The stripped product contained 2.17% nitrogen.

EVALUATION

The fuel additives were evaluated for their ability to maintain intake system cleanliness in the 10-hour Intake Valve Deposit Test. The engine used in this test is a Waukesha ASTM-CFR single-cylinder engine. Upon completion of the test the intake valve is removed, washed with hexane and weighed. The deposits are then removed with a wire brush and the valve reweighed. The difference between the two weights is the weight of deposit. Operating conditions include an engine speed of 1,800 rpm, a water temperature of 212° F (100° C), an air-fuel ratio of 14, and intake spark timing 15° BTC. All the following fuel composition examples contain 250 ppm of active additive and 1,000 ppm of a 1,700 SUS at 100° F (38° C) neutral petroleum oil as a carrier in a base fuel which is predominantly a Chevron gasoline. Fuel compositions are evaluated by comparing the number of mg of hexane washed deposits produced by the following fuel compositions with the number of mg of hexane washed deposits produced by the base fuel alone, or the base fuel containing 1,000 ppm of the above neutral petroleum oil.

EXAMPLE 1

A fuel composition containing polyisobutenyl-N,N',N'-trimethylethylene diamine wherein said polyisobutenyl substituent was of about 1,400 mw, in a base fuel which gave 112 mg of hexane washed deposits in the Intake Valve Deposit Test.

EXAMPLE 2

A fuel composition containing polyisobutenyl-N,N',N'',N'''-tetramethyl-tri (trimethylene) tetramine wherein said polyisobutenyl substituent was of about 1,400 mw, in the base fuel of Example 1.

EXAMPLE 3

A fuel composition containing polyisobutenyl cyclobiuret (diazodicarboximide of diethylene triamine) wherein said polyisobutenyl substituent was of about 1,400 mw, in a base fuel which gave 90 mg of hexane washed deposits in the Intake Valve Deposit Test.

EXAMPLE 4

A fuel composition containing polyisobutenyl aminoethyl phenylurea wherein said polyisobutenyl substituent was of about 1,400 average mw, in a base fuel which gave 83 mg of hexane washed deposits in the Intake Valve Deposit Test when it contained 1,000 ppm of the above neutral petroleum oil.

EXAMPLE 5

A fuel composition containing polyisobutenyl-bis-ethylene phenylurea wherein said polyisobutenyl substituent was of about 1,400 mw in the base fuel of Example 4.

EXAMPLE 6

A fuel composition containing polyisobutenyl-1-aminoethyl-2-oxoimidazolidine (cyclourea) wherein said polyisobutenyl substituent was of about 1,400 mw, in a base fuel which gave 176 mg of hexane washed deposits in the Intake Valve Deposit Test.

EXAMPLE 7

A fuel composition containing acetamide of polyisobutenyl ethylenediamine wherein said polyisobutenyl group was of about 1,400 average molecular weight, in the base fuel of Example 6.

EXAMPLE 8

A fuel composition containing polyisobutenyl aminoethyl phenylurea wherein said polyisobutenyl substituent was of about 1,400 mw, in a base fuel which gave 157 mg of hexane washed deposits in the Intake Valve Deposit Test when it contained 1,000 ppm of the above neutral petroleum oil.

TABLE I

| Fuel Composition | 10-hr CFR Intake Valve Deposit Test Washed Wt in mg |
|---|---|
| Example 1 | 63 |
| Example 2 | 54 |
| Example 3 | 11** |
| Example 4 | 8* |
| Example 5 | 35* |
| Example 6 | 10 |
| Example 7 | 12 |
| Example 8 | 54 |

*12-hour test on both fuel composition and base fuel.
**mean value

The data of Table I illustrates the effectiveness of the fuel additive of the present invention in controlling intake valve deposits. Examples 1 and 2 are included for comparison.

I claim:

1. A fuel composition comprising a major amount of a liquid hydrocarbon fuel and from 10 ppm to 4,000 ppm of a compound selected from the group consisting of hydrocarbyl phenyl urea, N-hydrocarbyl acetamide of ethylenediamine, and hydrocarbyl-1-aminoethyl oxoimidazolidone, wherein the hydrocarbyl groups contain from 30 to about 400 carbon atoms.

2. The composition of claim 1 wherein the hydrocarbyl group is a polyolefin derived from $C_2$-$C_6$ olefins.

3. The composition of claim 1 wherein the polyolefin is polybutene or polypropylene.

* * * * *